United States Patent [19]

Sumita et al.

[11] Patent Number: 5,030,391
[45] Date of Patent: Jul. 9, 1991

[54] PROCESS FOR THE PRODUCTION OF SPHERICAL PARTICLES OF CERAMICS

[75] Inventors: Masaya Sumita, Tokyo; Miyuki Kakinuma, Chiba, both of Japan

[73] Assignee: Asahi Kogaku Kogyo Kabushiki Kaisha, Tokyo, Japan

[21] Appl. No.: 243,712

[22] Filed: Sep. 13, 1988

[30] Foreign Application Priority Data

Sep. 14, 1987 [JP] Japan .................. 62-230748

[51] Int. Cl.$^5$ .............................. B29B 9/00
[52] U.S. Cl. .......................... 264/5; 264/4.3; 427/213.3
[58] Field of Search .............. 264/5, 7, 4.1, 4.3; 427/212, 213.36, 221, 212, 215, 213.3; 252/302, 304, 306, 309, 312

[56] References Cited

U.S. PATENT DOCUMENTS

| | | |
|---|---|---|
| 3,696,547 | 7/1976 | Isawa et al. . |
| 3,780,195 | 12/1973 | Balassa . |
| 3,943,063 | 3/1976 | Morishita et al. ............ 427/212 X |
| 3,943,115 | 3/1976 | Lawaguchi et al. . |
| 3,971,852 | 7/1976 | Brenner et al. . |
| 4,113,500 | 9/1978 | Ebihara et al. . |
| 4,149,894 | 4/1979 | Ebihara et al. . |

FOREIGN PATENT DOCUMENTS

| | | |
|---|---|---|
| 1433242 | 4/1976 | United Kingdom . |
| 2034678 | 6/1980 | United Kingdom . |
| 2175293 | 11/1986 | United Kingdom . |

*Primary Examiner*—Jan H. Silbaugh
*Assistant Examiner*—Christopher A. Fiorilla
*Attorney, Agent, or Firm*—Sandler, Greenblum & Bernstein

[57] ABSTRACT

A process for the production of spherical ceramics particles which are useful as a filling material for osseous defects, as a carrier for drug delivery system and as a packing material for a liquid chromatography includes the steps of forming a first spherical particle consisting of a particulate ceramics-based core and a shell of polymeric material covering the core by using microcapsule technology, and removing the shell from the first spherical ceramic particle to obtain the sperical particles.

18 Claims, 1 Drawing Sheet

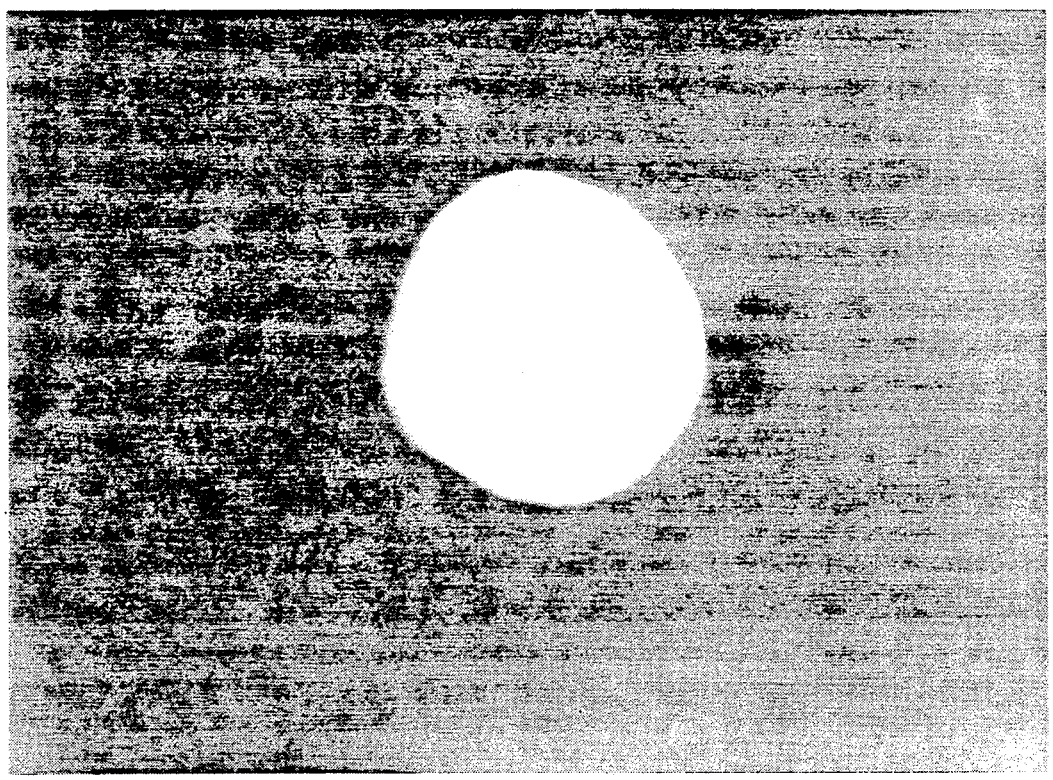
Fig _ 1

PROCESS FOR THE PRODUCTION OF SPHERICAL PARTICLES OF CERAMICS

BACKGROUND OF THE INVENTION

1. Field of the Invention

The present invention relates to a process for the production of spherical particles of ceramics. More particularly, the present invention relates to a novel process for the production of spherical, calcium phosphate-based ceramic particles which have a large diameter and a well defined roundness and therefore are particularly suitable as a filling material for osseous defects, as a carrier for drug delivery system and as a packing material for a liquid chromatography.

2. Description of Related Art

Calcium phosphate, especially hydroxylapatite has been found to be useful as a biomaterial such as osseous filling materials and as a packing material for a liquid chromatography. In fact, it has already been commercialized for these purposes.

Heretofore, hydroxylapatite used as a packing agent in a liquid chromatography has been comprised of irregularly shaped of particles, because those particles were produced by crushing. Recently, an improved packing agent using spherical hydroxylapatite has been developed. This improved packing agent exhibits a high resolution power and a good durability much superior to the resoltuion power and durability attainable by crushed hydroxylapatite particles. However, to attain a high flow rate in the liquid chromatography, it was necessary to increase the size of the particles of the filling agent.

Similarly, commercially available hydroxylapatite particles for use in implantation in vivo have been comprised of irregularly shaped particles because of the crushing employed in the production of those particles size. Particle of such particles has been about 100 $\mu$m. Such hydroxylapatite particles can be introduced into osseous defects such as those encountered in various periodontal diseases. Hydroxylapatite particles can be filled in gaps between the dentition and the maxilla or mandibula to cover the gingiva, or, soft tissues. This generally accomplished in this manner is because soft tissues of a human body may be damaged by sharp edges of said particle,s.

Other typical production process for spherical particles including spherical hydroxylapatite particles are generally designated a spray drying process and a high-speed agitation granulation process.

The particles produced by the spray drying process have a shape similar to that of the complete spheres. Accordingly, heretofore, almost of the commercially available spherical hxdroxylapatite particles have been produced by this process. However, since resulting particle size is increased by increasing scale of the devices used, it is essential to use large-scale devices, especially if it is desired to provide spherical hydroxylapatite particles having a diameter of 10 $\mu$m or more.

On the other hand, the high-speed agitation granulation process is characterized in that the particles of 100$\mu$m or more can be produced by a relatively small device. However, this process is not suited to produce spherical hydroxylapatite particles. This is because of certain specific physical properties (mainly, water adsorption property) of the particles which prevent hydroxylapatite them from acquiring a complete spherical shape during such a process.

SUMMARY OF THE INVENTION

An object of the present invention is to provide an improved process for the production of spherical ceramics particles which process allows production of ceramics particles having a relatively large size even when a small-scale device is used. Additionally, and it is an object of the present invention to allow production of a more completely rounded ceramics particles, compared with those produced by prior art processes without suffering from adverse effects of the physical properties of said particles.

According to the present invention, there is provided a process for the production of spherical particle of ceramics, characterized by comprising the steps of:
 forming a first spherical particle consisting of a particulate ceramics-based core and a shell of polymeric material covering said core by using a microcapsule technology, and removing said shell from said first spherical particle to obtain said spherical particles of ceramics.

According to the present invention, there is also provided a process for the production of spherical particles of ceramics, characterized by comprising the steps of:
 pouring an aqueous slurry of ceramics into a solution of water-insoluble polymeric resin in a hydrophobic solvent to form a water-in-oil type emulsion in which said aqueous slurry of ceramics in the form of spheres is being dispersed in said solution of the polymeric resin,
 pouring the resultant water-in-oil type emulsion in an aqueous phase to form a water-in-oil-in-water type emulsion in which spherical particles of said aqueous slurry of ceramics covered with a coating of said solution of the polymeric resin are being dispersed in said aqueous phase,
 solidifying said coating of said solution to form a shell of said polymeric resin covering said aqueous slurry of ceramics,
 separating the resulting spherical particles consisting of said aqueous slurry of ceramics, as a core, covered with said shell of said polymeric resin from said water-in-oil-in-water type emulsion, and
 baking said spherical particles to remove only said shell therefrom.

Using the production process according to the present invention, even if a small production equipment or device is used, ceramic particles having an increased particle size can be easily produced, while it was difficult to produce such large-sized particles in the prior art processes. Further, the shape of the thus produced ceramics particles is more close to that of completely rounded spheres, compared with the ceramics particles produced in accordance with the prior art processes. Therefore, the ceramics particles according to the present process may be well applied in various fields and are particularly useful as in vivo introduced materials such as osseous implants, as a carrier for the drug delivery system and as fillers for a chromatography.

BRIEF DESCRIPTION OF DRAWINGS

FIG. 1 is an optical microscopic photograph (magnification $\times$100) showing hydroxylapatite particles obtained in the Example 1 which will be described hereinafter with regard to the present invention.

DETAILED DESCRIPTION OF EMBODIMENTS

The production process of the spherical ceramics particles according to the present invention is characterized by covering a slurry of powdered ceramics as a core with a coating or outer shell of polymeric material such as polymeric resins by using a microcapsule technology to form first spherical particles having a core-shell structure, and then removing said shell from said first particles, for example, by baking said particles in an electric oven until said shell is burnt off.

As should be appreciated by those skilled in the art, the process of the present invention is novel and is based on an unique granulation mechanism which has not yet been suggested in the prior art, namely, combination of the formation of first spherical particles with a core-shell structure and the removal of the shell portion from the particles. Both of the formation of spherical particles and the removal of the shell portion from said particles can be effectively carried out by in different manners which will be described hereinafter with reference to preferred embodiments of the present invention.

In a preferred embodiment of the present invention, said first spherical particles having a core-shell structure are produced by dispersing an aqueous phase containing powdered ceramics, preferably an aqueous slurry of ceramics, in an oily phase containing the polymeric material, preferably polymeric resin to form a water-in-oil (W/O) type emulsion, dispersing said W/O type emulsion in another aqueous phase to form a water-in-oil-in-water W/O/W) type emulsion in which spherical particles of said ceramics-containing aqueous phase covered with a coating of said polymeric material-containing oily phase are being dispersed in said another aqueous phase, solidifying said polymeric material of said oily phase, and separating the resulting spherical particles of ceramics with a shell of hardened polymeric material from said W/O/W type emulsion.

In addition, in a preferred embodiment, the removal of the shell portion of the polymeric material from said first spherical particles is carried out by baking said spherical particles at an elevated temperature sufficient to cause decomposition and perfect combustion of said polymeric material, thereby burning off only said shell portion from said particles.

Generally speaking, when a hydrophobic or lipophilic substance is stirred in an aqueous solvent, it produces a plurality of droplets (oily droplets) like the complete sphere. In contrast, a hydrophilic substance, when stirred in a hydrophobic solvent, produces a plurality of droplets of water or aqueous material like the complete sphere. Moreover, when the hydrophobic solvent having dispersed therein spherical droplets of water is poured into and stirred in an aqueous solvent, it produces a so-called "W/O/W" type emulsion. This emulsion comprises the aqueous solvent having dispersed therein a plurality of droplets of so-called "W/O" type emulsion which each consists of the hydrophilic substance as a core and the hydrophobic substance as an outer shell. Namely, this route or method of the formation of the W/O/W type emulsion is used in the present invention.

In the production process of the present invention, as said hydrophobic or lipophilic substance, an oily phase containing the polymeric material is used, especially a solution of the water-insoluble polymeric material such as resins in a hydrophobic solvent. Also, as said hydrophilic substance, an aqueous phase containing powdered ceramics is used, especially an aqueous slurry of ceramics. First, said aqueous slurry of ceramics is added to said oily phase to prepare a W/O emulsion wherein said aqueous slurry is being dispersed as spherical particles like droplets of water in said oily phase. Second, the resultant W/O emulsion is added to an aqueous solvent to prepare a W/O/W emulsion wherein the spherical particles of said aqueous slurry covered with a coating of said oily phase are being dispersed in said aqueous solvent. Spherical particles which consist of said aqueous slurry of ceramics and which surfaces are coated with an outer shell of said oily phase are thus produced. While maintaining the above conditions, the polymeric resins contained in said oily phase are solidified in accordance with any conventional manner. After solidification of the outer shell, the spherical particles can be easily removed from said W/O/W emulsion, since they are now in the form of core-shell structure and their shell portion having filled therein said ceramics slurry is rigid. The separated spherical particles are then subjected to a baking step to cause a perfect combustion of the polymeric resins of the shell portion. As a result of burning off of said shell portion, desired spherical particles of ceramics are eventually obtained.

The water-insoluble polymeric resins used in the present invention include polystyrene, polyacrylate such as polymethyl methacrylate (PMMA) and other water-insoluble resins. Further, the hydrophobic solvents in which said polymeric resins are dissolved include a chlorinated hydrocarbon solvent such as dichloromethane, trichloroethylene and the like, and other hydrophobic solvents. When said polymeric resins are dissolved in said hydrophobic solvents to prepare an oily phase, content or concentration of said polymeric resins in said oily phase is preferably 5 to 25 w/v %. The content of said resins of less than 5 w/v % should be avoided, since when the hydrophobic solvent is evaporated or volatilized to harden said resins contained in the solvent, it becomes difficult to produce a shell-type coating of the resins capable of satisfactorily retaining therein said ceramics slurry without changing of the shape of the resin coating. Also, the content of said resins should not be over 25 w/v %. This is because such large content causes an increase of the viscosity of the oily phase. Therefore the formation of the W/O emulsion is hindered, when said aqueous slurry of ceramics is added to said oily phase.

The aqueous slurry of ceramics also used in the present invention can be prepared, for example, by dispersing powders of the selected ceramics in a hydrophilic solvent such as water and the like. The ceramics used in this preparation can be optionally selected from a variety of ceramics wellknown in the field. However, when the resulting spherical ceramics particles are intended to be used, for example, as a filler for osseous repair and as a packing for a liquid chromatography, it is especially preferred to use calcium phosphate or similar ceramics (these will be referred herein to as "calcium phosphate-based ceramics").

Further, in the preparation of the ceramics slurry, it is preferred to add an emulsifying agent such as gelatin and the like to the starting materials. Such addition of the emulsifying agent will assist a formation of good W/O emulsion after the aqueous ceramics slurry is poured into and stirred in the oily phase.

Using calcium phosphate as the ceramics material, said aqueous ceramics slurry can be produced in accordance with the following manner, presented as an example only: Calcium phosphate, after being dried in any method to prepare powders, is mixed with water. The mixture is then ground and blended in a ball mill, and is finally mixed with an emulsifying agent to produce a desired slurry of calcium phosphate. In this and other slurries of the present invention, a content or concentration of the solid is preferably in the range of 7 to 35 w/v %. The solid content of less than 7 w/v % will not result in a desired spherical product due to lesser amounts of ceramics powders to be included in shell of the polymeric resins, while the solid content of more than 35 w/v % will not provide a desired W/O/W emulsion, because excessively increased viscosity of the slurry makes agitation of the mixture too difficult.

The thus produced aqueous ceramics slurry is poured into said oily phase with stirring. While stirring is continued, the oily phase containing spherical droplets consisting of said ceramics slurry, namely, W/O emulsion is produced.

Thereafter, the W/O emulsion obtained in the previous step is poured in an aqueous phase with stirring. The aqueous phase used is preferably water or any water-based solvent. During stirring, a W/O/W emulsion in which spherical droplets of said slurry each coated with a layer of said oily phase are being dispersed in said aqueous phase. Also, preferably, the aqueous phase may additionally contain an emulsifying agent to improve dispersibility of said droplets therein, as in the production of the aqueous ceramics slurry.

After preparation of the W/O/W emulsion, said layer of the oily phase, particularly said polymeric resins contained in said layer is solidified. This can be effectively carried out, for example, by heating said emulsion while maintaining the dispersed conditions of the emulsion. As a result of heating, the solvent is volatilized from said layer of the oily phase covering said droplets of the ceramics slurry, and thus said polymeric resins are hardened. Heating should be made at a temperature high enough to cause volatilization of the solvent from said oily phase, and such a temperature is preferably in the range of 30° to 40° C., though it varies depending upon the solvent used. A temperature of less than 30° C. will require a long heating time of heating to attain complete volatilization of the solvent, a temperature of more than 40° c will cause undesirable defects such as softening or deformation of the polymeric resins.

The ceramics slurry with a hardened shell of the polymeric resins, namely, first spherical particles, is collected from said W/O/W emulsion with ease. To remove the shell portions, the first spherical particles are subjected to a decomposition treatment in which said shell portions are removed and spherical particles of ceramics remain. This decomposition treatment can be preferably carried out in an electic oven, for instance, by baking said first spherical particles at an elevated temperature sufficient to cause decomposition and perfect combustion of said polymeric resins constituting said shell portions, thereby burning off only said shell portions. The baking temperature is preferably 300° C. or more, because the temperature of less than 300° C. tends to produce residues of the organics onto a surface of the resulting spherical particles of ceramics. It should be noted that during this decomposition treatment, the aqueous solvent contained in the ceramics slurry is also evaporated.

The spherical particles of ceramics obtained may be used for the intended purposes, for example, as in vivo implants such as osseous implants or as a packing agent for a liquid chromatography, without further treatment. If desired, they may be additionally calcined at an appropriate temperature. In addition, when the spherical particles of ceramics have a configuration of the hollow particles, they may be used in the production of pharmaceutical preparations, namely, as a carrier for the drug delivery system.

The present invention will be further described with reference to typical working examples of the present invention. It should be noted that these examples do not restrict the scope of the invention.

EXAMPLE 1

Hydroxylapatite prepared in a wet synthesis process in accordance with a conventional method was used as a starting material in this example. The hydroxylapatite was spray dried to produce powdered hydroxylapatite. 200 g of water was added to 50 g of the powdered hydroxylapatite, and the mixture was ground for about 7 days in a ball mill. A slurry of the hydroxylapatite was thus prepared. To 20ml of this slurry, added and dissolved was 0.2 g of gelatin as an emulsifying agent, with heating.

Separately, 3 g of polystyrene having a molecular weight of about 400,000 was dissolved in 30ml of dichloromethane. To the resultant polystyrene solution, portion-wise added is 20ml of said slurry of the hydroxylapatite having dissolved therein gelatin, while continuing an intensive agitation with a propeller mixer. A W/O emulsion was produced.

The W/O emulsion was at once poured into an aqueous solution of gelatin, and the mixture was vigorously stirred for about 20 seconds with a propeller mixer. The aqueous solution of gelatin used herein has been previously prepared by dissolving 2 g of gelatin as the emulsifying agent in 200ml of water with heating, and retaining a liquid temperature at about 37° C. on a heater. A W/O/W emulsion was produced.

Thereafter, the W/O/W emulsion was gently stirred for about 3 hours, while maintaining a liquid temperature thereof at the range of 30° to 37° C. Dichloromethane was volatilized upon heating of the emulsion. After completion of volatilization, the remaining spherical particles were collected, classified with three sieves having a mesh size of 100 μm, 200 μm and 500 μm, respectively, and dried. The dried spherical particles for each mesh size weighed 0.175 g, 1.215 g and 1.245 g, respectively. These particles were then heated at 700° C. for about one hour in an electric oven. Spherical hydroxylapatite particles were obtained. FIG. 1 is an optical microscopic photograph (magnification ×100) showing the thus obtained hydroxylapatite particles having a particle size of about 200 μm.

EXAMPLE 2

Hydroxylapatite prepared in a wet synthesis process in accordance with a conventional method was used as a starting material in this example. The hydroxylapatite was spray dried to produce powdered hydroxylapatite. 200 g of water was added to 50 g of the powdered hydroxylapatite, and the mixture was ground for about 7 days in a ball mill. A slurry of the hydoxylapatite was thus prepared. To 20ml of this slurry, added and dissolved is 3 g of gelatin as an emulsifying agent, with heating.

Separately, 5.4 g of polystyrene having a molecular weight of about 400,000 was dissolved in 30ml of dichloromethane. To the resultant polystyrene solution, portion-wise added is 20ml of said slurry of the hydroxylapatite having dissolved therein gelatin, while continuing an intensive agitation with a propeller mixer. A W/O emulsion was produced.

The W/O emulsion was at once poured into an aqueous solution of gelatin, and the mixture was vigorously stirred for about 20 seconds with a propeller mixer. The aqueous solution of gelatin used herein had been previously prepared by dissolving 2 g of gelatin as the emulsifying agent in 200ml of water with heating, and retaining a liquid temperature at about 37° C. on a heater. A W/O/W emulsion was produced.

Thereafter, the W/O/W emulsion was gently stirred for about 3 hours, while maintaining a liquid temperature thereof at the range of 30° to 37° C. Dichloromethane was volatilized upon heating of the emulsion. After completion of volatilization, the remaining spherical particles were collected, classified with four sieves having a mesh size of 50 μm, 100 μm, 200 μm and 500μm, respectively, and dried. The dried spherical particles for each mesh size weighed 0.3 g, 0.32 g, 0.77 g and 0.15 g, respectively. These particles were then heated at 700° C. for about one hour in an electric oven. Spherical hydroxylapatite particles were obtained.

COMPARATIVE EXAMPLE

For a comparison purpose, this example describes use of a conventional high-speed agitation granulation process.

As in said Examples 1 and 2, hydroxylapatite prepared in a wet synthesis process in accordance with a conventional method was used as a starting material. The hydroxylapatite was spray dried to produce powdered hydroxylapatite.

The powdered hydroxylapatite was then subjected to a conventional high-speed agitation granulation process under the conditions described in the following Table 1. The results are summarized in the Table 1.

TABLE 1

| conditions & results | experiments | |
|---|---|---|
| | run No. 1 | run No. 2 |
| charge of ceramics powders | 2 kg | 1.5 kg |
| binder | 65%, based on ceramics powders, of aqueous solution of 2% polyvinyl alcohol | 60%, based on ceramics powders, of aqueous solution of 2% polyvinyl alcohol |
| result | wetted, but not granulated | increased load due to adhesion of powders onto the rotating blades, stop of agitation, not granulated |

We claim:
1. A process for the production of spherical ceramic particles, comprising the steps of:
    forming capsules comprising a particulate ceramic-based core and a shell of polymeric material covering said core by dispersing an aqueous phase containing powdered ceramics in an oily phase containing the polymeric material to form a water-in-oil type emulsion; dispersing said water-in-oil type emulsion in another aqueous phase to form a water-in-oil-in-water type emulsion containing capsules of said ceramic-containing aqueous phase covered with a coating of said polymeric material-containing oily phase dispersed in said another aqueous phase; solidifying said polymeric material of said oily phase; and separating the resulting capsules, each having a shell of hardened polymeric material from said emulsion; and
    removing said shell of polymeric material from said capsules to obtian said spherical ceramic particles.
2. The process according to claim 1, wherein said aqueous phase containing powdered ceramics is an aqueous slurry of ceramics.
3. The process according to claim 2, wherein said aqueous slurry of ceramics is a slurry of calcium phosphate.
4. The process according to calim 3, wherein a solid content of said calcium phosphate slurry is 7 to 35 w/v %.
5. The process according to claim 3, wherein said calcium phosphate slurry is prepared by adding water to powdered calcium phosphate to obtain a mixture, milling said mixture, to obtain a milled product, and mixing said milled product with an emulsifying agent.
6. The process according to claim 1, wherein said oily phase containing the polymeric material is a solution of a water-insoluble polymeric material in a hydrophobic solvent.
7. The process according to claim 6, wherein said water-insoluble polymeric material is selected from the group consisting of polystyrene, polyacrylate and other water-insoluble polymeric resins.
8. The process according to claim 6, wherein said hydrophobic solvent is a chlorinated hydrocarbon solvent.
9. The process according to claim 6, wherein a content of said water-insolule polymeric material in a solution thereof is 5 to 25 w/v %.
10. The process according to claim 6, wherein said coating of said polymeric material of said oily phase is solidified by heating said water-in-oil-in-water type emulsion at a high temperature which is sufficient to cause volatilization of said hydrophobic solvent from said oily phase.
11. The process according to claim 10, wherein said emulsion is heated at a temperature of from 30° C. to 40° C.
12. The process according to claim 1, wherein said shell of polymeric material is removed from each of said capsules by baking said capsules at an elevated temperature sufficient to cause decomposition and perfect combustion of said polymeric material, thereby burning off only said shell of polymeric material.
13. The process according to claims 1, which further comprises the step of calcinating the spherical ceramic particles after removing each said shell.
14. A process for the production of spherical ceramic particles comprising the steps of:
    pouring an aqueous slurry of ceramics into a solution of a water-insoluble polymeric resin in a hydrophobic solvent to form a water-in-oil type emulsion in which said aqueous slurry of ceramics in the form of spheres is dispersed in said solution of water-insoluble polymeric resin;
    pouring said water-in-oil type emulsion into an aqueous phase to form a water-in-oil-in-water type emulsion in which spherical particles of said aqueous slurry of ceramics covered with a coating of said solution of the polymeric resin are dispersed in said aqueous phase;

solidifying said coating of said solution to form a shell of said polymeric resin covering said aqueous slurry of ceramics;

separating the resulting spherical particles, each having a solidified coating forming a shell from said water-in-oil-in-water type emulsion; and baking said spherical particles to remove only said shell therefrom to obtain said spherical ceramic particles.

15. The process according to claim 14, wherein said aqueous slurry of ceramics is an aqueous slurry of calcium phosphate.

16. The process according to claim 15, wherein said aqueous slurry of calcium phosphate is prepared by adding water to powdered calcium phosphate to obtain a mixture, milling the mixture in a ball mill, and mixing the milled mixture with an emulsifying agent.

17. The process according to claim 15, wherein a solid content of said slurry of calcium phosphate is 7 to 35 w/v %.

18. The process according to claim 14, in which a content of said polymeric resin in said solution thereof is 5 to 25 w/v %.

* * * * *

UNITED STATES PATENT AND TRADEMARK OFFICE
CERTIFICATE OF CORRECTION

PATENT NO. : 5,030,391
DATED : July 9, 1991
INVENTOR(S) : Masaya SUMITA et al.

It is certified that error appears in the above-indentified patent and that said Letters Patent is hereby corrected as shown below:

Cover page, [56]References Cited, change "3,696,547" to ---3,969,547---.
    Cover page, [56]References Cited, change "Lawaguchi" to ---Kawaguchi---.
    Cover page, [57]Abstract, at line 9, change "sperical" to ---spherical ceramic---.
    At column 8, line 6 (claim 1, line 19), change "obtian" to ---obtain---.
    At column 8, line 13 (claim 4, line 1), change "calim" to ---claim---.
    At column 8, line 34 (claim 9, line 2), change "insolule" to ---insoluble---.
    At column 8, line 51 (claim 13, line 1), change "claims" to ---claim---.

Signed and Sealed this

Twenty-eight Day of February, 1995

Attest:

BRUCE LEHMAN

Attesting Officer     Commissioner of Patents and Trademarks